United States Patent [19]

Welker

[11] Patent Number: 4,922,764
[45] Date of Patent: May 8, 1990

[54] CONSTANT PRESSURE SAMPLE CYLINDER WITH SPHEROID MIXER

[75] Inventor: Brian H. Welker, Sugar Land, Tex.

[73] Assignee: Welker Engineering Company, Sugar Land, Tex.

[21] Appl. No.: 243,589

[22] Filed: Sep. 12, 1988

[51] Int. Cl.⁵ .............................................. G01N 1/10
[52] U.S. Cl. ................... 73/864.62; 73/863; 73/864.91; 73/DIG. 5
[58] Field of Search ........... 73/864.62, 864.91, 864.63, 73/863, DIG. 5; 366/140, 241; 52/172

[56] References Cited

U.S. PATENT DOCUMENTS

| | | | |
|---|---|---|---|
| 3,390,580 | 7/1968 | Taylor | 73/864.34 |
| 3,789,670 | 2/1974 | Rosenwald | 73/864.62 |
| 3,793,886 | 2/1974 | Rosenwald | 73/864.62 |
| 3,793,888 | 2/1974 | Rosenwald | 73/864.62 |
| 4,149,411 | 4/1979 | Fisher et al. | 73/863.58 X |
| 4,302,158 | 11/1981 | Brown | 417/559 X |
| 4,363,300 | 12/1982 | Honda | 92/177 X |
| 4,409,850 | 10/1983 | Zeck | 73/864.62 |
| 4,457,171 | 7/1984 | Grebauer | 73/DIG. 5 |
| 4,459,865 | 7/1984 | Welker | 73/864.62 |
| 4,628,750 | 12/1986 | Welker | 73/864.62 X |

*Primary Examiner*—Tom Noland
*Attorney, Agent, or Firm*—Gunn, Lee & Miller

[57] ABSTRACT

A constant pressure cylinder with a spheroid or ellipsoid mixer is disclosed herein. Improvements include a spheroid or ellipsoid mixing element for mixing the accumulated sample. The mixing element is free to move about the sample chamber but is consturcted in such a way to avoid damage to the interior cylinder walll. Other generally ellipsoid shaped mixing elements are also disclosed. The invention additionally incorporates an improved piston for use in the cylinder. The piston contains a magnet assembly which may be used in conjunction with an invention by a third party to visually display the location of the piston in the cylinder.

18 Claims, 2 Drawing Sheets

CONSTANT PRESSURE SAMPLE CYLINDER WITH SPHEROID MIXER

RELATED APPLICATION

The application relates to copending application Ser. No. 243,261, filed Sept. 12, 1988 entitled "Purge Valve" filed by Applicant.

BACKGROUND OF THE INVENTION

1. Field of the Invention

This invention relates to a constant pressure sample cylinder with spheroid or ellipsoid shaped mixing element. Other generally ellipsoid shaped mixing elements are also disclosed. These mixing elements are capable of mixing a sample in the sample chamber when the cylinder is manually inverted. The force of gravity urges the mixing element to move through the sample which creates vortices and general agitation of the sample. This turbulence causes stratified samples with different specific gravities to be mixed. Another feature of this invention is an improved piston for use in constant pressure sample cylinders. As is well known in the art, it is desirable to accumulate sample in a vessel at a relatively high pressure. The pressure of the vessel is relatively high for the express purpose of confining the sample, and in particular, to prevent the sample from changing phase from a liquid to a gas. The device is able to be filled with sample to a maximum design capacity for the device, typically several hundred cubic centimeters. Pressures as high as 2,000 psi are not extreme.

While the sample is being accumulated over a period of days or weeks, the sample typically will stratify. The sample tends to stratify because it is typically a heterogeneous mix of different hydrocarbons with different specific gravities. For example, production from a wet gas well may include the following: methane, propane, butane, isobutane, natural gasoline and/or ethane. Some of these hydrocarbons may liquefy at ambient conditions and are referred to in the industry as "light liquids".

When it is time to remove the sample from the constant sample pressure cylinder, it is first necessary to mix the sample. After mixing, a lab technician will then draw off a portion of the sample for analysis in a gas chromatograph or other suitable instrument. The Btu of the sample is then calculated based on the content analysis from the gas chromatograph. This disclosure features a spheroid or ellipsoid shaped mixing element. The mixing element is in the form of an untethered solid which churns the stored sample and thereby mixes it when the cylinder is manually inverted. Motion is imparted to the mixing element by gravity.

Other alternative embodiments of the mixing element include a shape comprising two circumferences joined by a radius at the perimeter. This alternative embodiment is not a true spheroid or ellipsoid; however it will function in approximately the same manner and will avoid damage to the interior walls of the cylinder.

The piston has a depression on its lower face to nest with the mixing element. This mixing element and piston configuration enables the piston to be initially forced by pressure at the time of charging to the extreme of its travel, capturing the ellipsoid mixing element and nesting against the head at the end of the storage cylinder. This design captures the mixing element. When the alternative embodiment mixing element is used, the depression in the lower face of the piston and the head is sized to conform to the shape of the alternative mixing element.

The mixing element is untethered in the sample chamber. However, the forces of gravity will bring the mixing element to the bottom of the chamber. Untethered mixing elements can be dangerous in that they are shaken violently at the time of mixing and such mixing elements may damage the finish on the interior wall of the surrounding cylinder. This spheroid or ellipsoid mixing element is designed with sufficiently rounded exterior surfaces so that they do not scratch or mar the interior surface finish of the cylinder when they come in contact during mixing. The piston slides along the cylinder, thereby requiring a high quality finish. The high quality finish must be preserved to avoid leakage around the piston. The ellipsoid shaped mixing element in the preferred embodiment is manufactured from Celcon M-90, Kel-F or other suitable nonmaring materials. Celcon M-90 is a thermoplastic manufactured by Celanese Chemical Company from acetal. Kel-F is a series of fluorocarbon products manufactured by 3M Company including polymers of chlorotrifluorethylene and certain copolymers that are characterized by high thermal stability, resistance to chemical corrosion, high dialectric strength, high impact, tensil and compressive strength.

2. Description of the Prior Art

U.S. Pat. No. 4,459,865, assigned to Welker Engineering Company, discloses a constant pressure cylinder with vortex mixer. This prior art device contains a tethered mixing element which is more expensive to manufacture and maintain than the untethered ellipsoid shaped mixing element of the present invention. In addition the present invention has an improved piston design over the aforementioned patent.

U.S. Pat. No. 4,409,850 assigned to Y-Z Industries, Inc. discloses a constant pressure cylinder with untethered spherical mixer. The spherical mixer disclosed in this prior art device has a diameter which is generally in excess of one half the diameter of the cylinder. The present invention has superior mixing capabilities because of the shape of the spheroid or ellipsoid mixing element over a round ball. Another relevant reference is U.S. Pat. No. 3,789,670 assigned to Cities Service Oil Company which discloses a round ball as a vortex mixer, said ball generally having a diameter at least about one fourth as large as the inside diameter of the cylinder. Again the present invention has superior mixing capabilities to this reference.

Some prior art pistons knows to applicant had a magnet assembly positioned at the very front of the piston which caused a hammering effect when said piston was forcibly driven against either end cap. After repeated hammering the magnet assembly cracked and fell apart which resulted in scoring on the interior diameter of the cylinder. The present invention provides a piston with a means for cushioning the magnet assembly which is superior to these prior art designs.

Another device of interest is U.S. Pat. No. 3,789,670 of Rosenwald. The same inventor is listed on additional U.S. Pat. Nos. 3,793,886 and 3,793,888. The earlier patent of McKinney U.S. Pat. No. 2,636,387 is also noted. An additional reference is U.S. Pat. No. 3,390,580 of Taylor. These references listed above are representative of devices over which the present application distinguishes.

BRIEF SUMMARY OF INVENTION

The present apparatus is an improved constant pressure cylinder and piston for storage of a sample. It is improved by incorporation of a modified piston apparatus. It is further improved by the spheroid or ellipsoid mixing element. The structure allows use of this invention with another structure, U.S. Pat. No. 4,457,171 which is a tracker device. The piston moves as sample accumulates, thereby causing the tracker as shown in U.S. Pat. No. 4,457,171 to visually display to an observer the position of the piston and the volume of the sample stored in the constant pressure cylinder. Another tracker device is shown in U.S. Pat. No. 4,459,865 and can also be used with this invention.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figures 1, 2:
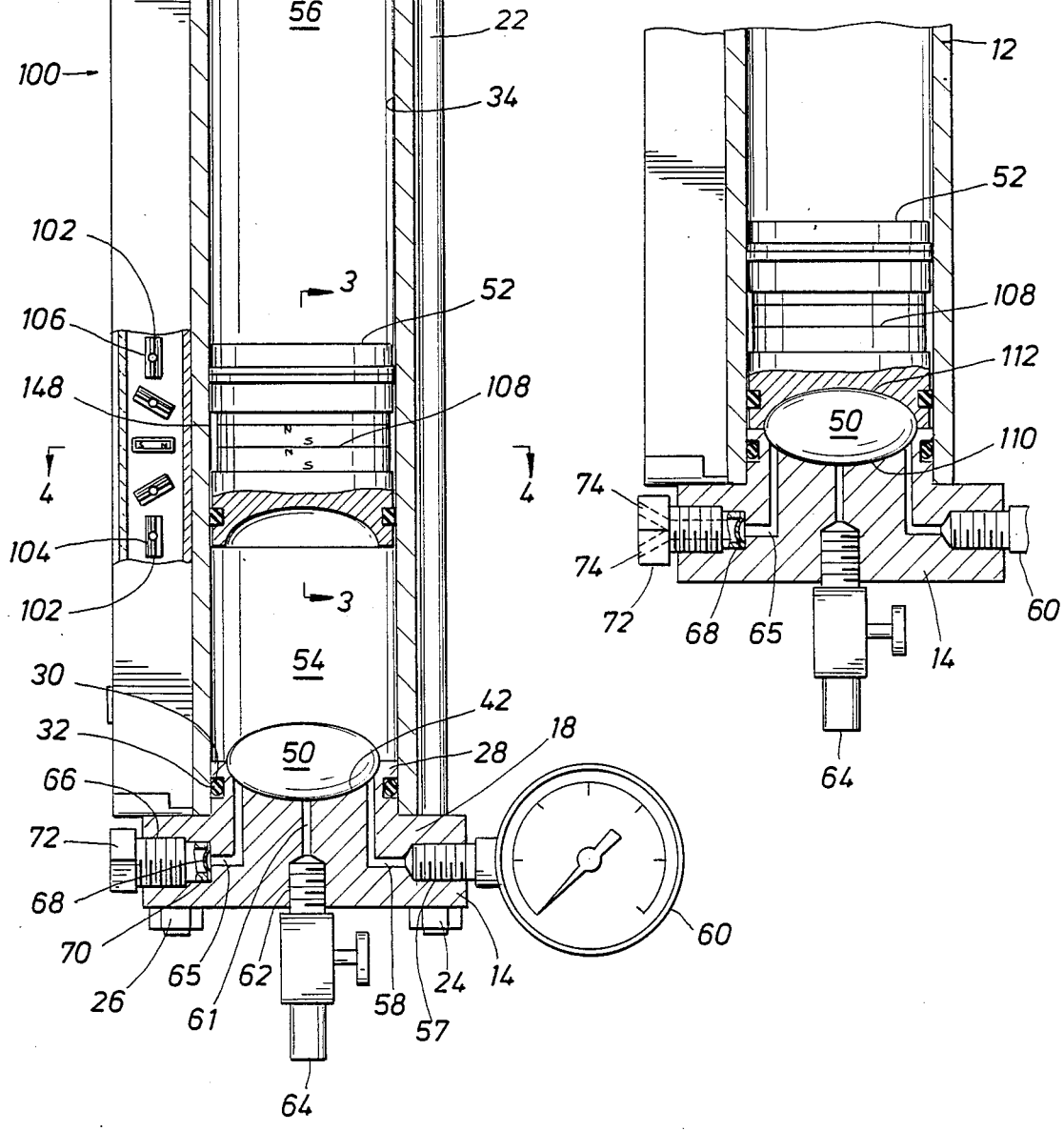
FIG. 1 is a section view of the improved constant pressure sample cylinder and piston constructed in accordance with the teachings of this disclosure. This figure also shows a partial section view of the tracker device disclosed in U.S. Pat. No. 4,457,171.
FIG. 2 is a section view of the piston and cylinder showing the piston nesting against the spheroid mixing element nesting against the head of the cylinder which is sometimes referred to as an end cap.

Attention is first directed to FIG. 1 of the drawing. There, a constant pressure cylinder 10 is comprised of an outer cylinder sleeve 12. It extends between a lower cylinder head or end cap 14 and a similar end cap or upper head 16. The lower head is constructed with a surrounding flange 18 and the upper head is likewise constructed with a surrounding flange 20. The flange 18 is constructed with a plurality of holes therein, said holes receiving a plurality of tie bolts 22. The flange 20 in upper head 16 has a plurality of threaded receptacles therein which receive the tie bolts 22. The tie bolts are secured by a plurality of nuts 24 and 26. This configuration enables the tie bolts 22 to extend the full length of the apparatus and surround the cylinder 12. The two heads 14 and 16 are pulled toward one another by tightening the plurality of bolts 24 and 26. A shoulder 28 is formed on the flange 18 and is sized to receive the cylinder 12. A channel 30 is cut in the shoulder 28 to receive O-ring 32. The O-ring 32 forms a seal with the interior diameter 34 of they cylinder 12. A shoulder 36 is formed on flange 20, said shoulder being sized to be positioned inside the cylinder 12. A channel 38 is cut circumferentially about the shoulder 36. An O-ring 40 fits in the channel 38. The O-rings 32 and 40 provide a seal for the cylinder 12 to prevent leakage therefrom.

The head 14 has an internal face 42 conforming in shape with the ellipsoid shaped mixing element 50. The piston 52 is slidably mounted and positioned inside the cylinder 12. The piston 52 in conjunction with the cylinder 12 and the lower head 14 define a sample chamber 54.

The piston 52 in conjunction with the cylinder 12 and the upper cap 16 define a precharge chamber 56.

The lower head is further constructed with a port 57 and an interior passage 58 which provides communication between the sample chamber 54 and the port 57. A pressure gauge 60 is installed in port 57. The pressure gauge 60 is designed to display the pressure within the sample chamber 54. Another interior passage 61 provides communication between the sample chamber 54 and a port 62. A valve 64 is installed in port 62. The valve 64 is normally closed during the sampling process to retain sample in the chamber 54. A third interior passage 65 provides communication between the sample chamber 54 and port 66. A burst disc 68 is installed in port 66. The burst disc is held in place by a washer 70 and a nut 72. The nut 72 is shown in section view in FIG. 2 showing internal passages 74 which allow pressure to be vented from the sample chamber 54 in the event the burst disc 68 ruptures.

The upper head 16 has a port 76 and an interior passage 77 which provides communication between the precharged chamber 56 and the port 76. A pressure gauge 78 is installed in port 76. The pressure gauge 78 is designed to display the pressure within the precharge chamber 56. The upper head 16 also has a port 80 and another interior passage 81 therein which provides communication between the precharge chamber 56 and the port 80. A valve 82 is installed in port 80 and is normally closed. The upper head 16 has another port 84 and a third interior passage 85 therein which provides communication between the precharge chamber 56 and the port 84. A burst disc 88 is placed in port 84 and is secured by a washer 90. The burst disc 88 and washer 90 are held in place by bolt 92. The interior configuration of bolt 92 is similar to the interior configuration of bolt 72 shown in FIG. 2.

The tracker device as disclosed in U.S. Pat. No. 4,457,171 is generally identified by the numeral 100. A plurality of markers 102 are aligned longitudinally in the tracker device 100. The markers 102 are typically colored on one side 104 and are white on the other side 106. As the piston 52 moves along the cylinder 12 the markers 102 are magnetically attracted to the magnet assembly 108 in the piston 52. The markers 102 rotate counter clockwise in response to the magnetic forces imparted by the magnet assembly 108. The markers 102 have magnets assembled therein as taught in the aforementioned patent which tend to hold them in place until they are rotated by countervailing magnetic forces such as those exerted by the magnet assembly 108 as the piston moves from end cap 14 towards end cap 16.

In FIG. 2 the piston 52 nestles against the spheroid shaped mixing element 50 which in turn nestles against the lower head 14. The lower head 14 has a spheroid shaped depression 110 sized to receive the mixing element 50. The piston 52 likewise has an spheroid shaped depression 112 which allows the nestling of the piston 52 the mixing element 50 and the lower head 14 as shown in FIG. 2. The bolt 72 which holds the burst disc 68 in place is shown in sectional view with an outlet port 74. If the burst disc ruptures, fluid can exhaust from the sample chamber 54 through the passage 65 to the port 66 and finally to atmosphere through the port 74 in the bolt 72.

Figure 3:
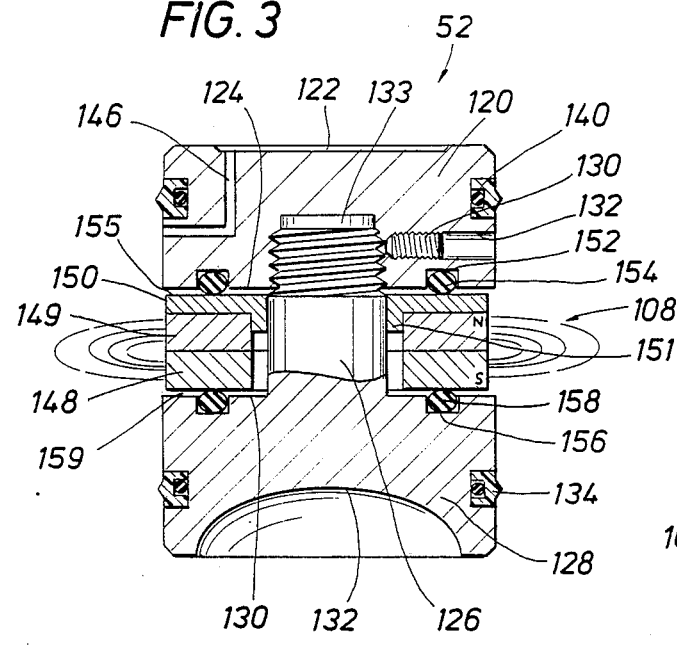
FIG. 3 is a section view of the piston taken along the line 3—3 of FIG. 1.

In FIG. 3 the piston is generally identified by the numeral 52 and the magnet assembly is generally identified by the numeral 108. The piston 52 is comprised of a first disc 120 which has a first face 122 and a second face 124. The first disc 120 has a threaded receptacle 133 therein. The piston 52 also consists of a second disc 128 which has a first face 130 and a second face 132. There is an elongate protrusion 126 formed in the first face 130 of the second disc 128. The receptacle 133 is sized to receive the elongate protrusion 126 extending from the second disc 128. The receptacle 133 is threaded as shown in the drawing to coact with the threads on the elongate protrusion thereby joining the first disc 120 with the second disc 128. As will be recognized by those skilled in the art there are various alternative methods for joining the first disc 120 with the second disc 128. It is within the scope of this invention to include a means for joining said first disc and said second disc such as a nut and bolt running completely through said first disc and said second disc. Another alternative means for joining which is within the scope of this invention is to place the elongate protrusion 126 on the first disc 120 and the receptacle 133 in the second disc 128.

Another alternative embodiment for joining the first disc 120 and the second disc 128 would be a locking screw 130 sized to fit in the bore 132. When the locking screw 130 is fully engaged with the elongate protrusion 126 it will join the first disc with the second disc. In this alternative embodiment, using the locking screw 130, it would not necessarily be essential to have threads on the elongate protrusion 126 or the receptacle 132.

The piston 152 has a crown seal 134 which is positioned circumferentially about the second disc 128. In the preferred embodiment the crown seal is composed of Fluorotrel manufactured by Micro Dot-Polyseal of Salt Lake City, Utah. The crown seal 134 can also be composed of Hytrel a thermoplastic manufactured by DuPont. Those skilled in the art will recognize that there are numerous other materials in addition to Hytrel which are suitable for manufacturing this seal. As will be readily appreciated by those skilled in the art there are alternative types of seal means other than the crown seal 134 which could affect a seal for this piston.

A bearing 140 is circumferentially positioned on the first disc 120. The purpose of the bearing 140 is to maintain the piston 152 in coaxial alignment inside the cylinder 12. The bearing means 140 and the seal means 134 align the piston 152 coaxially in the cylinder so that the piston does not scratch the cylinder. As a matter of manufacturing convenience the bearing 140 is a crown seal identical to the crown seal in 134; however, this is strictly a matter of convenience because the bearing means 140 does not perform a seal function. Instead it performs an alignment function. Those skilled in the art will readily understand that the crown seal 140 could contain notches therein and still provide the coaxial alignment essential to operation of the piston in the cylinder. Those skilled in the art will also readily understand that alternative types of bearing devices for example a plurality of buttons made out of an elastomeric substance positioned around the first disc would also provide the coaxial alignment function of bearing means 140.

An equalizing port 146 allows pressure in the precharge chamber 56 to communicate with the annular area 148 as shown in FIG. 1. This equalizing port is designed to prevent a locking between the seal 134 and the bearing 140. Obviously if the bearing 140 had serrations therein an equalizing port would not be necessary.

The magnet assembly 108 in the preferred embodiment is manufactured from circular donut shaped magnets constructed Alnico 5. Alnico is an alloy containing chiefly aluminum, nickel and cobalt; it has outstanding properties as a permanent magnet. A first magnet 148 is joined by epoxy cement or other suitable cement to a second magnet 149. The second magnet 149 is joined by epoxy cement or other suitable cement to a deflector ring 150. The deflector ring 150 is manufactured in the preferred embodiment of carbon steel. The deflector ring serves the purpose of deflecting the magnetic field and enhancing the strength of the two magnets as shown by the magnetic field lines in FIG. 3. If the deflector ring were not joined to the first and second magnets the magnetic field not be as intense or strong as the magnetic field achieved in FIG. 3 with the deflector ring.

A circular channel 152 is cut in the second face 124 of the first disc 120. An O-ring 154 is placed in the channel 152 and protrudes slightly beyond the second face 124 of the first disc 120. The O-ring 154 contacts the metal deflector ring 150 and provides a cushion space 155 between the metal ring 150 and the second face 124 of the first disc 120. The deflector ring 150 therefore does not come into mechanical contact with the second face 124 of the first disc 120. It will be noted that the deflector ring 150 is formed in such a way as to provide a shoulder 151 to provide contact with the elongate protrusion 126. The magnets themselves 148 and 149 do not come into contact with the elongate protrusion 126. The purpose of this configuration is to (a) separate the magnets from the elongate protrusion 126 and (b) to provide a precise alignment of the exterior diameter or the magnets 148 and 149 to ensure that they cannot scratch the inside diameter 34 of the cylinder 12. There is a second channel 156 cut in the first face 130 of the second disc 128. A second O-ring 158 is positioned in the second channel 156. The second O-ring 158 contacts the magnet 148 and provides a cushion space 159 between the first face 130 of the second disc 128 and the magnet 148. The purpose of the o-rings 154 and 158 is to provide a means for cushioning the magnet assembly 108. The o-rings 154 and 158 provide cushion spaces 155 and 159 between the first disc 120, the magnet assembly 108 and the second disc 128 thereby providing a means for cushioning the magnet assembly. This is particularly important because the Alnico magnets 148 and 149 are particularly brittle and can be easily fractured. On some occasions the piston 52 will be rapidly cycled back or forth so as to slam into the shoulder 28 of end cap 14 or the shoulder 36 of end cap 20. For example, lab technicians will sometimes slam the piston 52 against shoulder 28 of end cap 14 when filling the precharge chamber 56. This occurs if the valve 64 is fully opened prior to filling the precharge chamber 56. When the valve 64 is fully opened, the piston 52 is free to move rapidly in response to pressure when the precharge chamber 56 is filled. If there were no means for cushioning the Alnico magnets in the piston 52, they would after a period of rough treatment become cracked and fall off the piston. As the magnets degenerated there would be scarring of the interior surface 34 of the cylinder 12 which would ultimately cause a failure of the seal 134. This would require that the entire constant pressure sample cylinder be sent back to the plant for reconditioning. It is therefore particularly important to provide a means for cushioning the magnet assembly 108.

Figure 4:
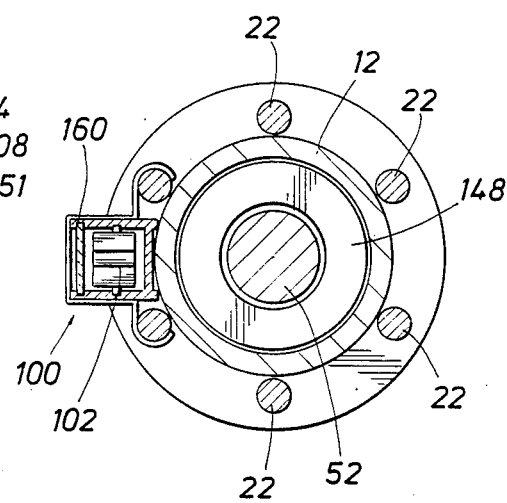
FIG. 4 is a sectional view of the piston cylinder arrangement and tracker device taken along line 4—4 of FIG. 1.

In FIG. 4 the piston 52, the cylinder 12, the stud bolts 22 and the tracker device 100 are shown in sectional view. The magnet 148 has attracted the marker 102 and has rotated it approximately 90 degrees counter clockwise. A clear viewing lens 160 allows an observer to look through the marker device 100 and look at the markers 102 to determine the location of the piston 52 in the cylinder 12.

Figure 5:
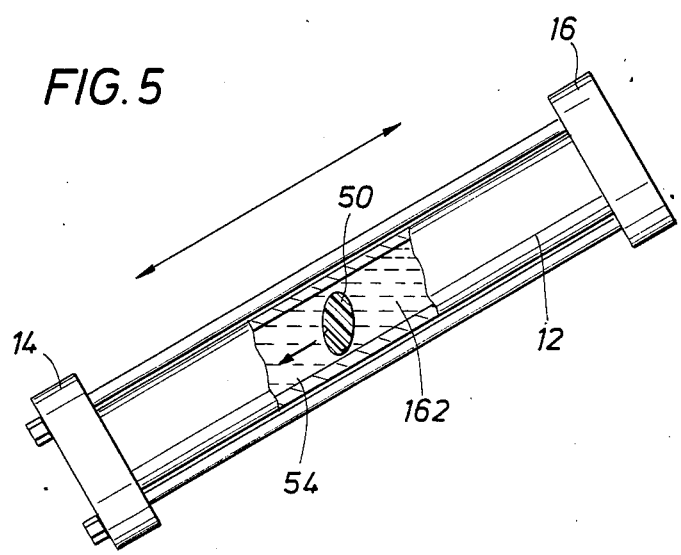
FIG. 5 is a partial section view of the piston cylinder of FIG. 1 at approximately a 45 degree angle, the preferred angle for mixing of the sample.

In FIG. 5 the cylinder 12 is shown at approximately a 45 degree angle in a position for mixing the sample 162 in the sample chamber 54. The spheroid shaped mixing element 50 is shown moving in the direction of the arrow being urged on by the forces of gravity through the sample chamber 54 towards the head 14. Eddies and vortices occur in the sample medium 162 behind the mixing element 50 as it moves through the mixing chamber 54. In the preferred embodiment an operator or lab technician will manually hold the constant pressure cylinder 10 in approximately a 45 degree angle with the upper head 16 elevated above the lower head 14. This will allow the forces of gravity to move the mixing element 50 in the direction of the arrow thus creating vortices and eddies in the sample 162. When the mixing element 50 contacts the lower head 14 the field operator or lab technician should again invert the constant pressure cylinder 10 so that the head 14 is raised above the head 16 again at approximately a 45 degree angle allowing the mixing element 50 to fall according to the forces of gravity through the sample chamber 54 into contact with the piston 52. This repeated inversion of the constant pressure cylinder 10 allows the mixing element 50 to move back and forth on a repeated basis causing agitation and mixing of the sample 162. Because of the unique design of the mixing element 50 it does not scar the interior diameter 34 of the cylinder 12.

Figure 6:
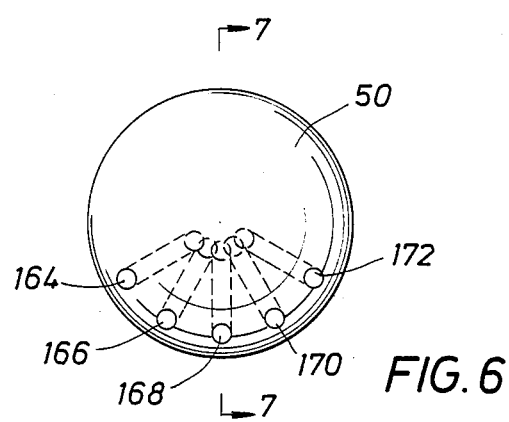
FIG. 6 is a top view of the spheroid shaped mixing element showing a plurality of weights in phantom view.

FIG. 6 shows a top view of the mixing element 50 with a plurality of weights 164, 166, 168, 170 and 172 shown in phantom.

Figure 7:
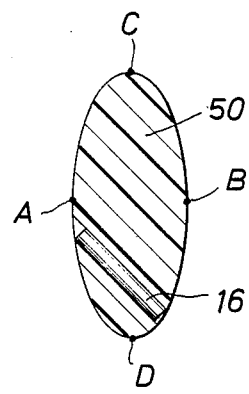
FIG. 7 is a section view of the spheroid shaped mixing element taken along line 7—7 of FIG. 6.

In FIG. 7 a cross sectional view of the mixing element 50 is shown along lines 7—7 of FIG. 6. The weight 168 is shown in the mixing element 50. Except for the weights in the mixing element 50 it is a solid body manufactured of Celcon M-90, Kel-F or other suitable nonmaring material which will not abrade, scar or otherwise damage the finish of the interior diameter 34 of the cylinder 12. Because of the plurality of weights in the mixing element 50 it has an offset center of gravity which generally causes it to move through the sample chamber 54 with the weights closest to the earth. It has been determined that a weighted mixing element is more advantageous than an unweighted mixing element for mixing liquids such as crude oil. An unweighted mixing element is suitable for mixing gases and/or light liquids.

The mixing element 50 can be an ellipsoid or a spheroid but not a sphere. An ellipsoid or spheroid generates more turbulence than a sphere and therefore has improved mixing qualities when compared with a sphere. The weighted ellipsoid or spheroid also passes through a sample medium more quickly than a sphere thus promoting more rapid mixing.

The mixing element 50 shown in FIGS. 6 and 7 is a spheroid. On one axis the section view is circular, as shown in FIG. 6 and on the opposite axis the section view is elliptical as shown in FIG. 7.

The mixing element 50 can also be an ellipsoid. In an ellipsoid both section views are elliptical.

Figure 8:
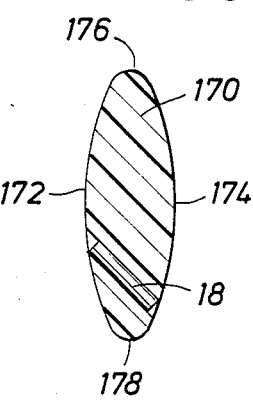
FIG. 8 is an alternative embodiment shown in section view of the mixing element which is not a spheroid or ellipsoid but can be functionally substituted therefore in the present invention.

FIG. 8 is a section view of an alternative embodiment of the mixing element which is not an ellipsoid or spheroid. The mixing element 170 of FIG. 8 is defined by two opposing circumferences 172 and 174. The edge of the mixing element 170 is defined by two opposing radiuses 176 and 178. Although the parimeter of the mixing element 170 does not satisfy the definition of an ellipsoid or spheroid, it is generally elliptical and within the scope of this invention. The edges of the mixing element 170 are sufficiently rounded to prevent scarring of the interior diameter 134 of the cylinder 12. A weight 180 is shown in mixing element 170. It is within the scope of this invention to also utilize unweighted mixing elements.

What is claimed is:
1. A sample storage apparatus comprising:
 (a) an elongate hollow cylinder having cylinder heads at both ends to close said cylinder;
 (b) a piston slidably mounted within said cylinder to divide said cylinder into first and second chambers, one chamber serving to receive a pressurized fluid and the other chamber adapted to receive sample through a passage in one of said cylinder heads and thereby comprising a sample chamber; and
 (c) a mixing element of generally ellipsoid shape having a size and shape to permit free movement of said element while mixing sample in said sample chamber.

2. The apparatus of claim 1 wherein said ellipsoid shaped mixing element comprises:
 (a) a solid ellipsoidal body having a circular edge smaller than the interior diameter of said cylinder;
 (b) said solid ellipsoidal body having at least one weight therein defining an offset center of gravity; and
 (c) in longitudinal cross section, said solid body defines an ellipse in the range of 20 to 35 degrees.

3. The apparatus of claim 1 wherein one of the cylinder heads has a face within said sample chamber, and said face is conformed to said generally ellipsoid shaped mixing element to enable facial contact and nesting between said generally ellipsoid shaped mixing element and said cylinder head face.

4. The apparatus of claim 3 wherein said face of said one of said cylinder heads defines a configuration corresponding to the configuration of said generally ellipsoidal mixing element.

5. The apparatus of claim 3 including a face on said piston in said sample chamber confronting said ellipsoid shaped mixing element, said face conforming to the shape of said ellipsoid shaped mixing element and said piston nesting on said ellipsoid shaped mixing element, and said mixing element nesting on said cylinder head face to substantially eliminate the volume of said sample chamber.

6. The apparatus of claim 1 wherein said mixing element is used in said cylinder, said mixing element comprising:
   (a) a solid body of generally ellipsoidal configuration having a circular edge smaller than the internal diameter of said cylinder; and
   (b) descent control means inducing a generally uniform path of free descent of said solid body through sample fluid contained within said sample chamber.

7. The apparatus of claim 6, wherein said descent control means is formed by weight means located in off-center relation to said solid body.

8. The apparatus of claim 1 wherein said piston can reciprocate in said cylinder, said piston comprising:
   (a) a first disc;
   (b) a second disc;
   (c) means for joining said first disc and said second disc;
   (d) a magnet assembly;
   (e) seal means positioned circumferentially about one of said first and second discs to prevent the passage of fluids past said seal means; and
   (f) bearing means positioned on one of said first and second discs for coaxial alignment of said piston within said cylinder.

9. The apparatus of claim 8 further including a port in said first disc to allow fluid pressure to equalize on both sides of said bearing.

10. The apparatus of claim 8 further including means for cushioning said magnet assembly between said first disc and said second disc.

11. The apparatus of claim 10 wherein said first disc defines a first face and a second face and said second disc defines a first face and a second face, and said magnet assembly confronts faces on said discs.

12. The apparatus of claim 11 wherein said means for cushioning comprises:
   (a) a first channel in said second face of said first disc;
   (b) a first O-ring sized to fit in said first channel and protrude beyond said second face of said first disc, said first o-ring providing a cushion space between said second face of said first disc and said magnet assembly;
   (c) a second channel in said first face of said second disc; and
   (d) a second O-ring sized to fit in said second channel, and protrude beyond said first face of said second disc, said second O-ring providing a cushion space between said first face of said second disc and said magnet assembly.

13. The apparatus of claim 8 further including an ellipsoid shaped depression in the second face of said second disc.

14. The apparatus of claim 8 wherein said means for joining comprises:
   (a) an elongate protrusion extending from said first disc and extending through said magnet assembly;
   (b) a receptacle formed in said second disc to receive said protrusion; and
   (c) internal threads formed in said receptacle and receiving external threads formed by said protrusion.

15. The apparatus of claim 8 wherein said means for joining comprises:
   (a) an elongate protrusion extending from said first disc and extending through said magnet assembly;
   (b) a receptacle formed in said second disc to receive said protrusion;
   (c) a threaded bore in said second disc connecting said receptacle to the exterior of said disc; and
   (d) a screw sized to coact with said bore, said screw contacting said protrusion and locking said protrusion said receptacle.

16. The apparatus of claim 8 wherein said magnet assembly comprises:
   (a) a first magnet;
   (b) a second magnet joined to said first magnet; and
   (c) a deflector element joined to second magnet.

17. The apparatus of claim 8 wherein said first disc and said second disc are non-ferrous materials.

18. A sample storage apparatus comprising:
   (a) an elongate hollow cylinder having cylinder heads at both ends to close said cylinder;
   (b) a piston slidably mounted within said cylinder to divide said cylinder into first and second chambers, one chamber serving to receive a pressurized fluid and the other chamber adapted to receive sample through a passage in one of said cylinder heads and thereby comprising a sample chamber; and
   (c) a mixing element of generally ellipsoid shape having a size and shape to permit free movement of said element while mixing sample in said sample chamber.
   (d) a magnet assembly mounted on said piston; and
   (e) magnetically actuated tracker means mounted on the exterior of said cylinder to visually display the location of said piston in said cylinder.

* * * * *